United States Patent [19]

Bohus et al.

[11] Patent Number: 4,806,151
[45] Date of Patent: Feb. 21, 1989

[54] BENZOIC ACID DERIVATIVES

[75] Inventors: Péter Bohus; Ferenc Bihari; Marianna Kertész née Szabó; István Küronya; Péter Boros; János Szulágyi; Jenö Mészáros, all of Budapest; Gyula Eifert, Dunakeszi; Agnes Mészáros née Szekrényes, Budapest; Ödön S. Jártoó, Budapest; László Gondos, Budapest, all of Hungary

[73] Assignee: Budapesti Vegyimüvek, Budapest, Hungary

[21] Appl. No.: 799,517

[22] Filed: Nov. 19, 1985

[30] Foreign Application Priority Data

Nov. 19, 1984 [HU] Hungary ............................ 4285/84

[51] Int. Cl.⁴ ............................................ A01N 37/44
[52] U.S. Cl. ......................................... 71/111; 71/115; 514/535; 514/568; 560/21; 560/22; 562/435; 562/437
[58] Field of Search ..................... 560/21, 22; 71/111, 71/115; 574/535

[56] References Cited

U.S. PATENT DOCUMENTS 3,257,190 6/1966 Soper .................................. 71/94 X

OTHER PUBLICATIONS

Summers, Chem. Abs., vol. 64, (1966), 8073(q)-8074(a).
Morozov et al., Chem. Abst., vol. 99, (1983), 6987(w).
Bowden et al., Jour. Amer. Chem. Soc., vol. 88 (1966), 949.

Primary Examiner—Michael L. Shippen
Attorney, Agent, or Firm—Schweitzer & Cornman

[57] ABSTRACT

According to the present invention there are provided fungicidal compositions comprising as active ingredient in an amount of 0.01–80% by weight a new benzoic acid derivative of the general Formula I

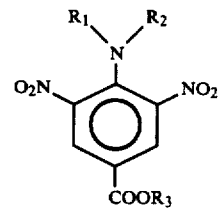

wherein
$R_1$ and $R_2$ stand for hydrogen, $C_{1-8}$ alkyl, $C_{2-8}$ alkenyl or benzyl;
$R_3$ represents hydrogen, $C_{1-8}$ alkyl or $C_{2-8}$ alkenyl;
$R_1$ and $R_2$ may be the same or different; and $R_3$ may be identical with or different from $R_1$ and/or $R_2$.

According to the present invention there is provided a process for the preparation of the compounds of the general Formula I which comprises esterifying 4-chloro-3,5-dinitro-benzoic acid with a saturated or unsaturated aliphatic alcohol at a temperature between 20° C. and 120° C.—preferably at 60°–100° C.—in the presence of a solvent as medium and in the presence of a catalyst, and aminating the ester thus obtained with ammonia or the corresponding primary or secondary amine at a temperature between 40° C. and 100° C.—preferably at 60°–90° C.—in the melt or in an inert solvent as medium, in the presence of an acid binding agent; or changing the order of succession of the said two steps and carrying out at first amination and thereafter esterification.

A preferred representative of the compounds of the general Formula I is the n-propyl-4-diallylamino-3,5-dinitro-benzoate.

13 Claims, No Drawings

BENZOIC ACID DERIVATIVES

This invention relates to new benzoic acid derivatives, a process for the preparation thereof, fungicidal and/or herbicidal compositions comprising the same and the use of the acid compounds for combating fungal diseases and/or weeds.

According to an aspect of the present invention there are provided new benzoic acid derivatives of the general Formula I

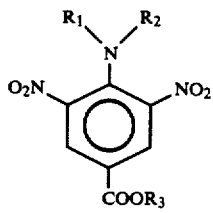

wherein
$R_1$ and $R_2$ stand for hydrogen, $C_{1-8}$ alkyl, $C_{2-8}$ alkenyl or benzyl;
$R_3$ represents hydrogen, $C_{1-8}$ alkyl or $C_{2-8}$ alkenyl;
$R_1$ and $R_2$ may be the same or different; and $R_3$ may be identical with or different from $R_1$ and/or $R_2$, *provided that* $R1$ and $R2$ are not hydrogen when $R3$ is hydrogen, methyl, ethyl, propyl or isopropyl.

A preferred representative of the compounds of the general Formula I is the n-propyl-4-diallylamino-3,5-dinitro-benzoate.

According to a further aspect of the present invention there are provided fungicidal and/or herbicidal compositions comprising as active ingredient in an amount of 0.01–80% by weight a compound of the general Formula I (wherein $R_1$, $R_2$ and $R_3$ have the same meaning as stated above) in admixture with suitable inert solid or liquid carriers, diluents and optionally other auxiliary agents.

The compounds of the general Formula I are useful fungicides and are active particularly against powdery mildew. Certain representatives of the compounds of the general Formula I possess significant herbicidal effect as well.

The compounds of the general Formula I may be formulated by known methods of pesticidal industry in usual forms such as emulsifiable concentrates (EC), suspension concentrates (SC), water-miscible solution concentrates (SL), wettable powder (WP), oily paste, granules (G), ultra-low volume solutions (ULV), foils, capsules etc.

The compounds of the general Formula I are new and the preparation thereof has never been described in prior art. The chemically most related known active ingredients are the 4-chloro-3,5-dinitro-benzoic acid esters. The fungicidal effect of the said compounds is disclosed in U.S. Pat. No. 2,841,521 and the herbicidal activity thereof is known from Japanese Pat. No. 78-10528.

In Hungarian Pat. No. 177,568 the use of the said compounds for seed dressing is disclosed. The widespread use of 4-chloro-3,5-dinitro-benzoic acid esters in plant protection is encountered however by a serious problem, namely the said compounds are phytotoxical against certain cultivated plants.

It is an object of the present invention to provide new benzoic acid derivatives suitable as fungicide and/or herbicide agents which do not cause any damages to the cultivated plants.

It is a further object of the present invention to provide a process for the preparation of the said compounds which is economically feasible on industrial scale too.

According to a further aspect of the present invention there is provided a process for the preparation of benzoic acid derivatives of the general Formula I (wherein $R_1$, $R_2$ and $R_3$ are stated above) which comprises esterifying 4-chloro-3,5-dinitro-benzoic acid or a halide—preferably chloride—thereof with a saturated or unsaturated aliphatic alcohol at a temperature between 20° C. and 120° C.—preferably at 60°–100° C.—in the presence of a solvent as medium and in the presence of a catalyst; and aminating the ester thus obtained with ammonia or the corresponding primary or secondary amine at a temperature between 40° C. and 100° C.—preferably at 60°–90° C.—in the melt or in an inert solvent as medium, in the presence of an acid binding agent; or changing the order of succession of the said two steps and carrying out at first amination and thereafter esterification.

The esterification reaction is carried out in an inert medium in the presence of a catalyst by using the corresponding saturated or unsaturated aliphatic alcohol.

Amination may be carried out in the melt or in an inert solvent in the presence of an acid binding agent, by using ammonia or the corresponding primary or secondary amine.

In the esterification step preferably a mineral acid or cation exchange resin may be used as catalyst. The solvent may be preferably excess of the esterifying alcohol or benzene, toluene, xylene or an other inert solvent may be applied. The reaction may be rendered complete preferably by removing the water formed in the reaction. This may be done by azeotropic distillation carried out with the esterifying alcohol or an inert solvent (e.g. benzene, toluene, xylene etc). If water is removed by means of azeotropic distillation with an inert solvent it is preferred to use 1.2–1.5 moles of the alcohol related to 1 mole of 4-chloro-3,5-dinitro-benzoic acid.

In the amination step an excess of the amine reactant may serve as acid binding agent or an other organic or inorganic base may be applied for this purpose. As organic base preferably triethyl amine and as inorganic base e.g. sodium or potassium hydroxide may be used. The amination reaction may be carried out in an inert organic solvent or in a mixture of water and a water-nonmiscible organic solvent. As inert organic solvent e.g. benzene, toluene, xylene or chloroform may be used. If an inorganic base is used as acid binding agent, the amination may be carried out in the presence of phosphoric acid or an acidic phosphate salt, in an aqueous melt or in a mixture of water and a water-nonmiscible organic solvent.

The molar ratio of the ester, amine and acid binding agent is preferably 1:1.0–1,2:1.0–1.2.

The fungicidal and/or herbicidal compositions of the present invention may be prepared by usual methods of pesticidal industry. The active ingredient content of the compositions depends on the mode of application and the formulation type and is in the range of 0.01–80% by weight.

As carrier solid carriers or liquid diluents may be used.

As solid carrier e.g. China-clay, attapulgit, montmorillonit, mica slate, pyrophillit, bentonite, diatomaceous earth, highly dispersed synthetic silicic acid, calcium carbonate, calcinated magnesium oxide, dolomite, gypsum, plaster of Paris, tricalcium phosphate, fuller's earth, ground tobacco leave stem, wood-flour etc. may be used.

Suitable liquid diluents are water, organic solvents and mixtures thereof, e.g. alcohols such as methanol, ethanol, n- and isopropanol, diacetone alcohol, benzyl alcohol; glycols e.g. ethylene glycol, triethylene glycol, propylene glycol; glycol esters e.g. methyl cellosolve; ketones e.g. acetone, methyl-ethyl-ketone, methyl-isobutyl-ketone, cyclopentanone, cyclohexanone; esters e.g. ethyl acetate, n- and isobutyl-acetate, amyl acetate, isopropyl miristate, dioctyl phthalate, dihexyl phthalate; aromatic, aliphatic and alicyclic hydrocarbons e.g. paraffin hydrocarbons, cyclohexane, kerosene, gasoline, benzene, toluene, xylenes, tetraline, dekaline; mixtures of alkyl benzenes; chlorinated hydrocarbons, e.g. trichloro ethane, dichloro methane, perchloro ethylene, dichloro propane, chloro benzene; lactones e.g. $\gamma$-butyrolactone; lactames e.g. N-methyl-pyrrolidone, N-cyclohexylpyrrolidone; acid amides e.g. dimethyl formamide; vegetable and animal oils e.g. sunflower oil, oliva oil, soya oil, castor oil and sperm oil etc.

As auxiliary agents wetting, suspensing, dispersing, emulsifying, antiaggregation agents, antiadhesives, anticaking agents, spreaders, agents improving infiltration, adhesives, antifoam agents and agents maintaining or improving the biological activity may be used.

The suitable wetting, dispersing, emulsifying agents, adhesives, antiaggregating agents and spreaders may be of ionic and non-ionic character.

As ionic agents salts of saturated or unsaturated carboxylic acids; sulfonates of aliphatic, aromatic and araliphatic hydrocarbons; sulfates of alkyl, aryl and aralkyl carboxylic acids, esters and ethers; sulfonates of condensation products of phenol, cresol and naphthalene; sulfatated vegetable and animal oils; alkyl and aralkyl phosphate esters and salts of the above compounds formed with alkali or alkaline earth metal or organic bases (e.g. amines, alkanol amines etc) may be used. Preferred derivatives of the said ionic surfactants are as follows: sodium lauryl sulfate, sodium-2-ethyl-hexyl-sulfate; the sodium, ethanol amine, diethanol amine, triethanol amine, and isopropyl amine salt of dodecyl benzene sulfonic acid; sodium mono- and diisopropyl naphthalene sulfonate; the sodium salt of naphthalene sulfonic acid; sodium diisooctyl sulfosuccinate; sodium xylene sulfonate; the sodium or calcium salt of petroleum sulfonic acid, soaps; sodium, calcium, aluminium or magnesium stearate etc. may be used. The phosphate esters may be phosphatated alkyl phenols or ethers of fatty alcohols formed with polyglycols and derivatives thereof partially or completely neutralized with the above cations of organic bases.

Suitable anionic surfactants are the disodium-N-octadecyl-sulfosuccinate, sodium-N-oleyl-N-methyl-tauride and various lignosulfonates.

Suitable non-ionic wetting, dispersing and emulsifying agents are the ethers of ethylene oxide formed with $C_{10-20}$ alcohols, e.g. stearyl-poly(oxyethylene), oleyl-poly(oxyethylene); ethers formed with alkyl phenols, e.g. poly(glycolethers) of tert. butyl, octyl and nonyl phenol; esters of organic acids, e.g. esters of stearic acid and miristic acid formed with polyethylene glycol or polyethylene glycol oleate etc; block polymers of ethylene oxide and propylene oxide; partial esters of fatty acids and oleic acid e.g. esters of sorbitol formed with oleic acid or stearic acid; condensation products of the above compounds formed ethylene oxide; tertiary glycols e.g. 3,6-dimethyl-4-octin-3,6-diol or 4,7-dimethyl-5-decin-3,7-diol; polyethylene glycol thioethers e.g. ether of dodecyl mercaptane formed with polyethylene glycol etc.

Suitable adhesives are the alkaline earth metal soaps, salts of sulfosuccinic acid esters, natural and artificial water soluble molecules e.g. caseine, starch, vegetable gums, gummi arabicum, cellulose ethers, methyl cellulose, hydroxyethyl cellulose, polyvinyl pyrrolidone, polyvinyl alcohol etc.

Suitable antifoam agents are poly(oxyethylene) and poly(oxypropylene) block polymers of low molecular weight; octyl-, nonyl and phenyl-poly(oxyethylene)—the number of ethylene oxide units >5; long chained alcohols e.g. octyl alcohol and special silicon oils, etc.

According to a preferred embodiment of the present invention there are provided fungicidal compositions in the form of emulsifiable concentrates (EC), suspension concentrates (SC) or wettable powders (WP) comprising n-propyl-4-diallylamino-3,5-dinitro-benzoate as active ingredient.

The composition of plant protecting agents comprising n-propyl-4-diallyl-amino-3,5-dinitro-benzoate as active ingredient is disclosed in Table 1.

TABLE 1

| Emulsifiable concentrates | 300 EC | 500 EC |
|---|---|---|
| Active ingredient | 300 g/l | 500 g/l |
| Tensiofix B 7438 | 80 g/l | 50 g/l |
| Tensiofix B 7453 | 20 g/l | 50 g/l |
| Xylene | ad 1 liter | ad 1 liter |
| Cyclohexanone | — | 300 ml |

| Suspension concentrates | 350 SC | 500 SC |
|---|---|---|
| Active ingredient | 350 g/l | 522 g/l |
| Ethylene glycol | 100 g/l | 80 g/l |
| Tensiofix XN6 | 30 g/l | — |
| Wettol D1 | 20 g/l | — |
| Aerosil 200 | 5 g/l | — |
| HOE S 1494 | — | 60 g/l |
| Rhodopol 23 | 2 g/l | 1 g/l |
| Silicon SRE | 5 g/l | 5 g/l |
| Ion-exchanged water | ad 1 liter | ad 1 liter |

| Wettable powder | 25 WP | 70 WP |
|---|---|---|
| Active ingredient | 25% | 70% |
| Ultrasyl VN3 | 10% | 20% |
| HOE S 1494 | 2% | 5% |
| Borresperse NA | 5% | — |
| Tinovetin B | 2% | 5% |
| China-clay | ad 100% | — |

The emulsifiable concentrates may preferably comprise xylene or a mixture of xylene and cyclohexanone as liquid diluent; calcium dodecyl benzenesulfonate and a condensation product of nonyl phenol and ethylene oxide or propylene oxide (Tensiofix B 7438 and Tensiofix B 7453) as emulsifier.

The suspension concentrates may preferably comprise ion exchanged water as liquid diluent; ethylene glycol as antifreezer; silicon oil emulsion as antifoam agent; xanthan gum type polysacharide (Rhodopol 23) as thickening agent; natural silicic acid anhydride (Aerosil 200) as anticaking component; Wettol DL as wetting agent; nonyl phenol polyglycol ether and a phosphatated derivative thereof (Tensiofix XN6) or the sodium sulfonate of a condensation product of cresol and formaldehyde (HOE S 1494) as dispersing and emulsifying agent.

The wettable powders may preferably comprise China-clay or artificial aluminium hydrosilicate (Ultrasyl VN3) as solid carrier; the sodium salt of diisobutyl naphthalene sulfonic acid (Tinovetin B) as wetting agent; the sodium sulfonate of the condensation product of cresol and formaldehyde (HOE S 1494) and sodium lignosulfonate (Borresperse NA) as dispersing agent.

According to a preferred form of realization of the process of the present invention n-propyl-4-diallylamino-3,5-dinitro-benzoate may be prepared by reacting 1 mole of 4-chloro-3,5-dinitro-benzoic acid with 1.25 moles of n-propanol at a temperature between 85° C. and 90° C., in the presence of a sulfuric acid catalyst, whereby the water formed is removed by azeotropic distillation with benzene. The distillation of water having been completed (5–7 hours) the reaction mixture, is cooled and the n-propyl-4-chloro-3,5-dinitro-benzoate is isolated. This compound is reacted with a 1.1 molar amount of diallyl amine at a temperature between 70° C. and 80° C., in an aqueous melt in the presence of 0.1 mole of 75% phosphoric acid and 1.05 moles of a 10% sodium hydroxide solution as acid binding agent. The reaction mixture is allowed to sedimentate, the organic phase is poured into water and the crystalline n-propyl-4-diallylamino-3,5-dinitro-benzoate is isolated.

According to a further aspect of the present invention there is provided a method for combating Fungi and/or weed pests which comprises applying onto the plants, parts thereof, the corn, the soil or onto the objects to be protected a composition are disclosed above.

The advantage of the compositions of the present invention resides in the fact that they are particularly effective against powdery mildew, constitute a valuable enrichment of the selection of available plant protecting agents and can be safely used in a number of cultivated plants. Our widespread tests carried out on the field and in orchard have shown that the compositions of the present invention are more effective than the commercially available fungicidal agents useful to combat powdery mildew and do not damage the cultivate plants.

The process of the present invention enables the economical manufacture of the compounds of the general Formula I on industrial scale and produces the said compounds with high yield in very pure form.

Further details of the present invention are to be found in the following Examples without limiting the scope of protection to the said Examples.

(A)

PREPARATION OF COMPOUNDS OF THE GENERAL FORMULA I

EXAMPLE 1

Laboratory scale preparation of methyl-4-chloro-3,5-dinitro-benzoate

Into a 250 ml round-bottomed flask equipped with a stirrer, thermometer and reflux condenser 74 g (0.3 mole) of 4-chloro-3,5-dinitro-benzoic acid, 128 g (4.0 mole) methanol and 14 g of concentrated sulfuric acid are introduced. The reaction mixture is refluxed under stirring for 8 hours, whereupon it is cooled to room temperature. The precipitated desired compound is filtered off, washed with 20 ml of cold methanol and dried. Thus 74.2 g of the desired compound are obtained, yield 95%, purity 99%.

In an analoguous manner ethyl-4-chloro-3,5-dinitro-benzoate is prepared too.

EXAMPLE 2

Laboratory scale preparation of n-propyl-4-chloro-3,5-dinitro-benzoate

Into a 1000 ml round-bottomed flask equipped with a stirrer, thermometer and Marcusson-condenser 180 g (3 moles) of n-propanol, and 380 g of benzene are weighed in, whereupon 493 g (2 moles) of 4-chloro-3,5-dinitrobenzoic acid and 20 g of concentrated sulfuric acid are added under stirring. The reaction mixture is heated to boiling on a water bath under stirring (86° C.) until no more water is distilled off. The water thus formed is collected in the Marcusson-condenser and removed if necessary. In the meantime the upper benzene/n-propanol phase is continuously re-introduced into the flask. The reaction having been completed the mixture is cooled to room temperature under stirring, the precipitated crystals are filtered off, washed with cold n-propanol and dried. Thus 490 g of the desired compound are obtained, yield 85%, purity 98%.

In an analoguous manner the following compounds are prepared:
isopropyl-4-chloro-3,5-dinitro-benzoate,
sec.butyl-4-chloro-3,5-dinitro-benzoate,
tert.butyl-4-chloro-3,5-dinitro-benzoate,
n-amyl-4-chloro-3,5-dinitro-benzoate,
n-octyl-4-chloro-3,5-dinitro-benzoate.

EXAMPLE 3

Pilot-plant scale preparation of n-propyl-4-chloro-3,5-dinitro-benzoate

Into a 50 l enamelled double-walled apparatus equipped with a stirrer and adjusted to azeotropic distillation 7.5 kg (0.125 kmole) of n-propanol, 19 kg of benzene, 25 kg (0.1 kmole) of 4-chloro-3,5-dinitro-benzoic acid and 1 kg of concentrated sulfuric acid are weighed in. The reactor is closed and the content thereof is heated to boiling by means of steam heating. The reaction mixture is heated to boiling (86°–90° C. until no more water leaves the system while the organic phase (a mixture of benzene and n-propanol) is continuously reintroduced into the reactor. Once the distillation of water is completed (5–7 hours) the mixture is cooled below 20° C., the precipitated crystals are isolated by centrifugation, washed with cold benzene and dried. Thus 25.4 kg of the desired compound are obtained, yield 88%, purity 97%.

EXAMPLE 4

Laboratory scale preparation of ethyl-4-di-n-propylamino-3,5-dinitro-benzoate in chloroform Into a 1000 ml round-bottomed flask equipped with a stirrer, reflux condenser and thermometer 360 ml of chloroform are weighed in, whereupon 137.3 g (0.5 mole) of ethyl-4-chloro-3,5-dinitro-benzoate are added. The reaction mixture is warmed to 40° C. and 126.3 g (1.25 mole) of di-n-propyl amine are added within half an hour. The reaction mixture is refluxed for 3 hours, cooled, the precipitated di-n-propylamine hydrochloride is filtered off. The chloroform solution is washed with water, diluted with hydrochloric acid and finally with water and evaporated to dryness. Thus 166 g of the desired compound are obtained, yield 98%, purity 95%.

In an analoguous manner the following compounds are prepared by using the excess of the corresponding amine as acid binding agent:
methyl-4-di-n-propylamino-3,5-dinitro-benzoate,
methyl-4-diallylamino-3,5-dinitro-benzoate,
methyl-4-(ethyl-2-methyl-allyl-amino)-3,5-dinitro-benzoate,
ethyl-4-diallylamino-3,5-dinitro-benzoate,
ethyl-4-(ethyl-2-methyl-allylamino)-3,5-dinitro-benzoate,
n-propyl-4-amino-3,5-dinitro-benzoate,
n-propyl-4-methylamino-3,5-dinitro-benzoate,
n-propyl-4-dimethylamino-3,5-dinitro-benzoate,
n-propyl-4-diethylamino-3,5-dinitro-benzoate,
n-propyl-4-di-isopropylamino-3,5-dinitro-benzoate,
n-propyl-4-diallylamino-3,5-dinitro-benzoate,
n-propyl-4-(ethyl-2-methyl-allylamino)-3,5-dinitro-benzoate,
n-propyl-4-di-n-butylamino-3,5-dinitro-benzoate,
n-propyl-4-dibenzylamino-3,5-dinitro-benzoate,
isopropyl-4-diethylamino-3,5-dinitro-benzoate,
sec.butyl-4-di-n-propylamino-3,5-dinitro-benzoate,
tert.butyl-4-dimethylamino-3,5-dinitro-benzoate,
tert.butyl-4-diethylamino-3,5-dinitro-benzoate,
tert.butyl-4-di-n-propylamino-3,5-dinitro-benzoate,
n-amyl-4-di-n-propylamino-3,5-dinitro-benzoate,
n-octyl-4-propylamino-3,5-dinitro-benzoate,
n-octyl-4-n-butylamino-3,5-dinitro-benzoate,
n-octyl-4-n-hexylamino-3,5-dinitro-benzoate,
n-octyl-4-n-octylamino-3,5-dinitro-benzoate,
n-octyl-4-dimethylamino-3,5-dinitro-benzoate,
n-octyl-4-diethylamino-3,5-dinitro-benzoate,
n-octyl-4-di-n-propylamino-3,5-dinitro-benzoate,
n-octyl-4-diallylamino-3,5-dinitro-benzoate,
n-octyl-4-di-n-butylamino-3,5-dinitro-benzoate,
n-octyl-4-dibenzylamino-3,5-dinitro-benzoate.

In an analoguous manner to Example 4 the following compounds are prepared except that 1.05 mole of amino and 1.05 mole of triethyl amine acid binding agent are used for 1 mole of ethyl-4-chloro-3,5-dinitro-benzoate.
n-propyl-4-n-propylamino-3,5-dinitro-benzoate,
n-propyl-4-n-butylamino-3,5-dinitro-benzoate,
n-propyl-4-n-hexylamino-3,5-dinitro-benzoate,
n-propyl-4-n-octylamino-3,5-dinitro-benzoate.

EXAMPLE 5

Laboratory scale preparation of isopropyl-4-di-n-propylamino-3,5-dinitro-benzoate by using an aqueous sodium hydroxide solution as acid binding agent Into a 2000 ml round-bottomed flask equipped with a reflux condenser, stirrer and thermometer 730 ml of xylene, 288.5 g (1 mole) of isopropyl-4-chloro-3,5-dinitro-benzoate and 300 g of water are introduced. The reaction mixture is warmed to 60° C. and 106 g (1.05 mole) of di-n-propylamine are added within an hour at such a rate that the temperature should be maintained by cooling at 65°-70° C. To the mixture 11.5 g (0.1 mole) of 85% phosphoric acid are added whereupon 440 g of a 10% sodium hydroxide solution (1.1 mole) are added dropwise at 65°-70° C. within an hour. The reaction mixture is stirred for a further hour, cooled to 25° C. and allowed to stand. The phases are separated, the xylene layer is wwashed with tap water, allowed to stand again, and the phases are separated. Thus the xylene solution of the desired compound is obtained, yield 96%, purity 98%. The solution needs no further purification and can be directly used for the production of an emulsifiable concentrate.

EXAMPLE 6

Pilot-plant scale production of n-propyl-4-diallylamino-3,4-dinitro-benzoate by aminating in the melt Into a 250 l enamelled double-walled autoclave equipped with a reflux condenser, stirrer, thermometer and feeding stud 100 kg of water and 60 kg (0.208 kmole) of n-propyl-4-chloro-3,5-dinitro-benzoate are weighed in. The mixture is warmed to 70° C. under stirring and 22 kg (0.227 kmole) of diallylamine are added within an hour at such a rate that the temperature should be maintained by cooling at 75°-80° C. To the reactor 1.2 kg of 75% phosphoric acid (0.01 kmole) are added and thereafter 86 kg of a 10% sodium hydroxide solution (0.215 kmole) are added within an hour at a temperature of 75°-80° C. The reaction mixture is stirred for a further hour, and allowed to stand until warm (70° C.). The phases are separated, the lower organic phase is poured into 100 of water under constant cooling and stirring. The mixture is cooled below 20° C. and the crystallized product is centrifuged and dried. Thus 71 kg of the desired compound are obtained, yield 97.8%, purity 98.5%.

(B)
TESTING OF BIOLOGICAL ACTIVITY OF THE COMPOUNDS OF THE GENERAL FORMULA I

EXAMPLE 7

Determination of activity against *Erisyphe graminis tritici* in glasshouse

The activity against *Erysiphe graminis tritici* (wheat powdery mildew) is tested on the cultivated plant type "Kavkáz". 50 wheat corns are sown into each cultivating dish. The plants are infectead at two-leaved stage by applying fresh conidia from the infected wheat onto the wheat previously sprayed with the test compound and onto the control wheat. After infection the plants are placed into a humid chamber for 48 hours. The fungus coverage of the plants and the development of the colonies is evaluated continuously in a semi-quantitative manner. The precental protective effect is related to the infection % of the control. In Table 2 the results evaluated on the 8th day after infection are disclosed. The active ingredient concentration of the spray amounts to 75, 150, 300, 600, 1200, 2400, 4800, 9600 an 19200 ppm, respectively.

As standard pyrazophos and tiophanat-methyl are used in the same dose range. The percental protecting effect of the various concentrations of the sprays is evaluated by means of the probit method (relationship between dose and effect). In Table 2 the active ingredient concentrations (ppm) belonging to the probit 5 (=50% protecting effect) and probit 6 (=84% protecting effect) values are disclosed. Some of the test compounds show a slight phytotoxicity at a concentration of 4800 ppm or above this level, but the wheat tolerates the initial scorching being 15% or below this value.

TABLE 2

| Effectivity data against *Erysiphe graminis tritici* | | | |
|---|---|---|---|
| Test compound | $ED_{50}$ (ppm) | $ED_{84}$ (ppm) | damages of wheat % |
| n-propyl-4-dimethylamino- | 1000 | 2000 | 10 |

TABLE 2-continued

Effectivity data against *Erysiphe graminis tritici*

| Test compound | ED$_{50}$ (ppm) | ED$_{84}$ (ppm) | damages of wheat % |
|---|---|---|---|
| 3,5-dinitro-benzoate | | | |
| n-propyl-4-diethylamino-3,5-dinitro-benzoate | 1200 | 3300 | — |
| n-propyl-4-di-n-propylamino-3,5-dinitro-benzoate | 600 | 2300 | 10 |
| n-propyl-4-diallylamino-3,5-dinitro-benzoate | 520 | 1500 | 15 |
| n-propyl-4-di-n-butylamino-3,5-dinitro-benzoate | 600 | 4000 | 10 |
| n-propyl-4-dibenzylamino-3,5-dinitro-benzoate | 3000 | 16000 | — |
| n-propyl-4-propylamino-3,5-dinitro-benzoate | 700 | 2800 | 20 |
| n-propyl-4-butylamino-3,5-dinitro-benzoate | 1100 | 2100 | 8 |
| n-propyl-4-hexylamino-3,5-dinitro-benzoate | 2600 | 10000 | 5 |
| n-propyl-4-octylamino-3,5-dinitro-benzoate | 3000 | 12000 | 5 |
| tert.butyl-4-diethylamino-3,5-dinitro-benzoate | 1050 | 4300 | 15 |
| tert.butyl-4-di-n-propyl-amino-3,5-dinitro-benzoate | 850 | 2550 | 20 |
| n-octyl-4-dimethylamino-3,5-dinitro-benzoate | >19200 | ∞ | — |
| n-octyl-4-diethylamino-3,5-dinitro-benzoate | 5400 | 19000 | 40 |
| n-octyl-4-di-n-propyl-amino-3,5-dinitro-benzoate | 5700 | 16000 | 10 |
| n-octyl-4-diallylamino-3,5-dinitro-benzoate | 16000 | ∞ | — |
| n-octyl-4-di-n-butyl-amino-3,5-dinitro-benzoate | 10000 | ∞ | 15 |
| n-octyl-4-dibenzylamino-3,5-dinitro-benzoate | 500 | 2000 | 20 |
| n-octyl-4-n-propylamino-3,5-dinitro-benzoate | >19000 | ∞ | 10 |
| n-octyl-4-n-butylamino-3,5-dinitro-benzoate | >19000 | ∞ | 5 |
| n-octyl-4-n-hexylamino-3,5-dinitro-benzoate | 6000 | ∞ | — |
| n-octyl-4-n-octylamino-3,5-dinitro-benzoate | 2000 | ∞ | — |
| ethyl-4-di-n-propylamino-3,5-dinitro-benzoate | 465 | 1040 | — |
| isopropyl-4-di-n-propyl-amino-3,5-dinitro-benzoate | 420 | 890 | — |
| sec.butyl-4-di-n-propyl-amino-3,5-dinitro-benzoate | 375 | 1300 | — |
| n-amyl-4-di-n-propylamino-3,5-dinitro-benzoate | 3550 | 10000 | — |
| 4-di-n-propylamino-3,5-dinitro-benzoic acid | ∞ | ∞ | — |
| pyrasophos | 450 | 12000 | 10 |
| thiophanat-methyl | 900 | 2000 | 10 |

EXAMPLE 8

Activity against *Sphaerotheca fuliginea* in glasshouse

The activity against *Sphaerotheca fuliginea* (cucumber powdery mildew) is carried out on cultivated plant type "Rajnai fürtös". In the test five weeks' old plants being at the stage of runner formation are used; the cucumber plants are pinched back to two leaves. One plant is placed into each cultivating dish and five replicates are used. The plants are treated with sprays having an active ingredient concentration of 111, 333, 1000 and 3000 ppm, respectively. The spray is allowed to dry and the treated and control plants are infected with a spore suspension the day after treatment. The spray and spore suspension [18–22 spores/10×16 sight field] are applied onto the surface of the leaves with the aid of a laboratory sprayer.

In Table 3 the percental protecting effect related to the control and measured on the 10th day after infection are disclosed. Simultaneously the rate of phytotoxicity (%) is evaluated, too.

TABLE 3

Activity against *Sphaerotheca fuliginea*

| | Average of five replicates | | |
|---|---|---|---|
| Test compound | conc. (ppm) | protecting effect (%) | scorching (%) |
| ethyl-4-di-n-propylamino-3,5-dinitro-benzoate | 111 | 55 | — |
| | 333 | 87 | — |
| | 1000 | 100 | — |
| | 3000 | 100 | — |
| isopropyl-4-di-n-propylamino-3,5-dinitro-benzoate | 111 | 30 | — |
| | 333 | 50 | — |
| | 1000 | 75 | 5 |
| | 3000 | 100 | 10 |
| n-propyl-4-di-n-propylamino-3,5-dinitro-benzoate | 111 | 81 | — |
| | 333 | 95 | — |
| | 1000 | 100 | — |
| | 3000 | 100 | 15 |
| sec.butyl-4-di-n-propyl-amino-3,5-dinitro-benzoate | 111 | 81 | — |
| | 333 | 87 | — |
| | 1000 | 92 | — |
| | 3000 | 100 | — |
| n-propyl-4-di-n-butylamino-3,5-dinitro-benzoate | 111 | 81 | — |
| | 333 | 95 | — |
| | 1000 | 100 | — |
| | 3000 | 100 | 10 |
| n-propyl-4-diallylamino-3,5-dinitro-benzoate | 111 | 67 | — |
| | 333 | 81 | — |
| | 1000 | 100 | — |
| | 3000 | 100 | 15 |
| tert.butyl-4-diallyl-amino-3,5-dinitro-benzoate | 111 | 50 | — |
| | 333 | 75 | — |
| | 1000 | 92 | 50 |
| | 3000 | — | 100 |
| n-propyl-4-n-propylamino-3,5-dinitro-benzoate | 111 | 30 | 15 |
| | 333 | 87 | 30 |
| | 1000 | — | 90 |
| | 3000 | — | 100 |
| thiophanat-methyl | 111 | 67 | — |
| | 333 | 81 | — |
| | 1000 | 100 | — |
| | 3000 | 100 | 10 |
| pyrasophos | 111 | 55 | — |
| | 333 | 98 | — |
| | 1000 | 100 | — |
| | 3000 | 100 | 5 |

The test is carried out by incubating the plants after infection in a humid chamber at 15°–18° C. for 24 hours. The spores are removed with water from the infected leaves and counted by using a microscope.

EXAMPLE 9

Activity against *Erysiphe betae* in glasshouse

The activity against *Erysiphe betae* (sugar beet powdery mildew) is determined on cultivated plant type "Beta-Poly M-102" at a 5–7 leaved stage. Two weeks after artificial infection 70–80% of the front side of the leaves and 20–40% of the backside thereof is covered by powdery mildew. The plants are treated with a spray having an active ingredient concentration of 2000 ppm in five replicates. From the 11 test compounds of the general formula I used n-propyl-4-diallylamino-3,5-dinitro-benzoate proved to be the most effective. As result of the use of the said test compound within six days after spraying the powdery mildew coverage of the leaves decreased by 83% and the remaining conidia became incapable of germination.

EXAMPLE 10

Activity tests on field and in orchard

The results of the tests carried out on field and in orchard are summarized in Tables 4–9. During the said tests no phytotoxicity was observed.

TABLE 4

Protection against *Leveilulla taurica* on paprika type "tomato-formed green of Szentes"

| Test compound | conc. of spray (%) | infected leaf surface (%) | stem infection (%) |
|---|---|---|---|
| n-propyl-4-diallylamino-3,5-dinitro-benzoate | 0.10 | 27.7 | 55 |
| tert.butyl-4-di-n-propyl-amino-3,5-dinitro-benzoate | 0.10 | 31.2 | 70 |
| methyl-4-dimethylamino-3,5-dinitro-benzoate | 0.10 | 29.3 | 62 |
| thiovit 80 WP | 0.30 | 36.5 | 56 |
| Untreated control | — | 63.4 | 95 |

The tests are carried out on parcels having a plot size of 4×6 m. After the appearance of the symptoms of infection the plants are sprayed every 7th day 3 times. In Table 4 the infection data measured on the 7th day after the last treatment are disclosed.

TABLE 5

Protection against *Erysiphe umbelliferarum* on parsley type "Berlini felhosszu"

| Test compound | Infected leaf surface (%) |
|---|---|
| n-propyl-4-di-n-butylamino-3,5-dinitro-benzoate | 8.6 |
| sec.butyl-4-di-n-butylamino-3,5-dinitro-benzoate | 7.1 |
| n-propyl-4-di-n-octylamino-3,5-dinitro-benzoate | 8.4 |
| thiophanat methyl | 7.3 |
| Untreated control | 39.8 |

The test is carried on parcels having a plot size of 5.1 m. After the appearance of the symptoms of infection the plants are treated with a spray having an active ingredient content of 0.15% every 14th day 3 times. In Table 5 the infection values measured on the 21st day after the last spraying are set forth.

TABLE 6

Protection against *Phodosphaera leucotricha* on apple-tree type "Jonathan"

| Test compound | 1. evaluation infected shoots (%) | 1. evaluation infectedness (%) | 2. evaluation infected shoots (%) | 2. evaluation infectedness (%) |
|---|---|---|---|---|
| sec.butyl-4-di-n-propyl-amino-3,5-dinitro-benzoate | 45 | 8.5 | 36 | 12.0 |
| n-propyl-4-di-n-propyl-amino-3,5-dinitro-benzoate | 38 | 5.2 | 27 | 9.2 |
| ethyl-4-di-n-propylamino-3,5-dinitro-benzoate | 36 | 6.6 | 20 | 5.4 |
| Thiovit 80 WP | 38 | 9.3 | 46 | 10.8 |
| Untreated control | 100 | 32.6 | 100 | 19.5 |

Streatment is repeated from spring to automn every 10th–14th day 11 times by using a spray having an active ingredient content of 0.15%. In Table 6 infectedness data determined at the end of the shooting period are disclosed.

TABLE 7

Protection against *Uncinula necator* on grapes, type "Olaszrizling"

| Test compound | Conc. of spray (%) | Time of evaluation | Ratio of infected bunches (%) |
|---|---|---|---|
| n-propyl-4-di-n-butyl-amino-3,5-dinitro-benzoate | 0.15 | 24. July | 4.5 |
| | | 26. August | 9.6 |
| | | 14. Sept. | 8.4 |
| sec.butyl-4-di-n-propyl-amino-3,5-dinitro-benzoate | 0.15 | 24. July | 8.7 |
| | | 26. August | 9.9 |
| | | 14. Sept. | 9.0 |
| Thiovit 80 WP | 0.30 | 24. July | 18.5 |
| | | 26. August | 20.2 |
| | | 14. Sept. | 14.6 |

In Table 7 the results of tests carried out in vineyards cultivated by the Mozer method and planted 11 years ago are summarized. Spraying is repeated in the summer months every 10th–14th day 8 times. The treatments serve simultaneously as protection against grape peronospora and grape moth as well.

TABLE 8

Protection against *Sphaerothica pannosa* on peach trees, type "Champion"

| Test compound | Time of evaluation | Infectedness of fruits (%) | Infectedness of leaves (%) |
|---|---|---|---|
| sec.butyl-4-di-n-propylamino-3,5-dinitro-benzoate | 25. May | 5.9 | — |
| | 26. July | 5.1 | 5.3 |
| n-propyl-4-di-n-butylamino-3,5-dinitro-benzoate | 25. May | 3.8 | — |
| | 26. July | 4.2 | 2.9 |
| Untreated control | 25. May | 19.4 | — |
| | 26. July | 15.2 | 36.4 |

Treatment is carried out between the end of April and the middle of July about every fortnight, totally 6 times by using a spray having an active ingredient content of 0.15%. In Table 8 the infectedness data measured at the third (25th May) and fifth (26th July) treatment are disclosed.

TABLE 9

Protection against *Spaerotheca mors uvae* on black currant type "Silvergieter"

| | I. | | II. | | III. | |
|---|---|---|---|---|---|---|
| | evaluation | | | | | |
| Test compound | fh % | f % | fh % | f % | fh % | f % |
| n-propyl-4-n-propyl-amino-3,5-dinitro-benzoate | 3.9 | 0.6 | 6.5 | 1.5 | 10.2 | 2.5 |
| n-propyl-4-di-n-propylamino-3,5-dinitro-benzoate | 4.5 | 0.8 | 9.2 | 2.0 | 12.5 | 3.1 |
| n-propyl-4-diallyl-amino-3,5-dinitro-benzoate | 4.7 | 0.9 | 8.5 | 2.1 | 11.2 | 3.0 |
| Thiovit 80 WP | 2.5 | 0.4 | 5.0 | 1.3 | 14.0 | 3.1 |
| Untreated control | 35.5 | 24.1 | 50.2 | 41.5 | 79.5 | 54.3 |

In Table 9 the following abbreviations are used:
fh % = percental ratio of infected shoots;
f % = infectedness %.

The tests are carried out on four years' old currant plots planted in rowed arrangement. With each test compound 10 bushes are sprayed, twice before and three times after gathering the fruit (16th April, 12th May, 22nd August, 2nd September, 18th September). In Table 9 the infectedness values determined on the 4th July (I. evaluation), 21st August (II. evaluation) and 8th October (III. evaluation) are disclosed.

In addition to the outstanding activity against powdery mildew, the compounds of the general Formula I are effective against other Fungi strains too, moreover they exhibit a certain herbicidal effect as well. It has been found—among others—that n-propyl-4-amino-3,5-dinitro-benzoate is active against *Aspergillus niger* and *Helminthiosporum turcicum*. As herbicide the compounds of the present invention are effective e.g. against Hungarian millet, particularly when applied in a pre-emergent manner.

(C)

PREPARATION OF THE COMPOSITIONS OF THE PRESENT INVENTION

EXAMPLE 11

Preparation of an emulsifiable concentrate (concentration 300 g/l)

Into an enamelled vessel equipped with a mantle and a propeller stirrer (20 l) 5000 g of xylene are introduced whereupon 800 g of Tensiofix B 7438 and 200 g of Tensiofix B 7453 emulsifiers are dissolved under constant stirring. The emulsifying agents are homogenized before used by heating at 60° C. and the warm mixture is added to xylene. To the solution containing the emulsifier 3130 g of technical grade (95.8%) n-propyl-4-diallylamino-3,5-dinitro-benzoate are added and stirring is continued until a transparent clear solution is obtained. The active ingredient content is adjusted to the concentration of 300 g/l at 20° C. by adding 682 g of xylene (20° C.). The solution is then filtered through a filter (pore size 0.2 micrometer).

EXAMPLE 12

Preparation of an emulsifiable concentrate (active ingredient content 500 g/l)

Into an enamelled vessel (20 l) equipped with a stirrer and a heatable-coolable mantle 4500 g of cyclohexanone and 200 g of xylene are introduced and a mixture of 750 g Tensiofix B 7438, and 750 g Tensiofix B 7453 emulsifiers is added; the emulsifying agents are homogenized by heating to 60° C. before addition. To the solution comprising the emulsifiers 7830 g of technical grade (95.8%) finely powdered n-propyl-4-diallylamino-3,5-dinitro-benzoate are added. Stirring is continued for about 2 hours until a clear transparent solution is obtained. The active ingredient content is adjusted to 500 g/l by adding 200 g of xylene to the solution (temperature 20° C.) and the solution is finally filtered through a suitable filter (pore size 0.2 micrometer).

EXAMPLE 13

Preparation of a suspension concentrate; active ingredient content 350 g/l)

Into a stainless vessel (40 l) equipped with a dissolver-disc stirrer and a coolable-heatable mantle 9000 g of ion-exchanged water and 200 g of ethylene glycol are introduced. In this mixture 450 g of Tensiofix XN 6—pre-heated to 50° C. and homogenized—are dissolved under constant stirring. To the solution thus obtained 300 g of powdered Wettol D1 are added and stirring is continued at 50° C. until a clear transparent solution is obtained. The content of the vessel is cooled below 20° C. and 5475 g of technical grade (95.8%) powdered n-propyl-4-diallylamino-3,5-dinitro-benzoate and 75 g of Aerosil are added.

75 g of Silicon 5RE and 1275 g ion-exchanged water are admixed in a glass and 300 g of the antifoam agent mixture thus obtained are added to the suspension of the active ingredient. The suspension thus obtained is introduced into a corund disc mill at a rate of 80 kg/hour (type Fryma MK 95); in the mill the N/P corund discs are arranged at a distance of 100 micrometers. To the pre-ground suspension thus obtained 150 g of the above antifoam-agent are added and the mixture is subjected to fine grinding in a horizontal closed pearl mill (type Dyno KD 5); the mill contains 4 liters of glass pearl grinding bodies having a diameter of 1-1.5 mm. Grinding is continued under intensive cooling (the temperature of the suspension should not exceed 40° C.) and continuous circulation until the average particle diameter is below 5 micrometers (The average particle diameter is determined by using a Coulter Counter TA-II particler analyser).

To the ground suspension the residual antifoam agent mixture and a solution of 30 g of Rhodopol 23 thickening agent and 300 g of ethylene glycol are added. Stirring is continued for a further hour.

EXAMPLE 14

Preparation of a suspension concentrate (active ingredient content 500 g/l)

In a 500 ml glass 18 g of Hoe S 494 dispersing agent are dissolved in a mixture of 150 g of ion-exchanged water and 24 g of ethylene glycol. To the clear solution thus obtained 157 g of technical grade (95.8%) ground n-propyl-4-diallylamino-3,5-dinitro-benzoate are added and the suspension formed is introduced into a pearl mill (type Molinex PE 75) and homogenized for 5 minutes by using a dissolver-disc stirrer. Grinding is carried out for 90 minutes at 1500 r.p.m., under vigorous stirring and by using 250 ml of glass pearl grinding bodies (diameter 1 mm). The grinding bodies are removed with the aid of a sieve (0.3 mm) and to the suspension obtained a solution of 1.5 g of Silicon SRE and 10 g of ion-exchanged water (antifoam agent) and 0.3 g of Rhodopol 23 thickening agent swollen in 7 g of ion-exchanged water are added and stirring is continued for 30 minutes by using a dissolver-disc stirrer.

EXAMPLE 15

Preparation of a 25% wettable powder

Into a Lödige N 20 type mixer 1647 g of China-clay and 300 g of Ultrasil VN 3 are introduced, the carrier mixture is homogenized for 2 minutes, whereupon 783 g of technical grade (95.8%) finely ground n-propyl-4-diallylamino-3,5-dinitro-benzoate are added. The mixture is stirred for 5 minutes, whereafter 150 g of Borresperse NA and 60 g of Hoe S 1494 dispersing agent are added. The mixture is stirred for 5 minutes, whereupon 60 g of Tinovetin B wetting agent are added. The mixture is homogenized for 3 minutes and ground twice in a mill (type Alpine C-160; feeding rate 2 kg/hour). The ground product is homogenized in a Lödige M20 mixer for 3 minutes.

EXAMPLE 16

Preparation of a 70% wettable powder 16.9 g of Ultrasil VN3, 73.1 g of technical grade (95.8%) finely ground n-propyl-4-diallylamino-3,5-dinitro-benzoate, 5 g of Hoe S 1494 dispersing agent and 5 g of Tinovetin B wetting agent are homogenized. The mixture thus obtained is subjected to pre-grinding in a INA-10S type mill equipped with rotating knives for 30 seconds and the mixture thus obtained is subjected to fine-grinding in a mill (type JMRS-80) under a grinding air-pressure of 5 bar and an injector pressure of 4.9 bar.

What we claim is:

1. Fungicidal and/or herbicidal composition comprising as active ingredient in an amount of 0.01–80% by weight a new benzoic acid derivative of the general Formula I

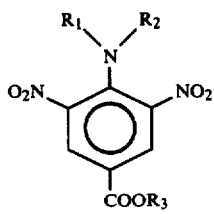

wherein
  $R_1$ and $R_2$ stand for $C_{1-8}$ alkyl, $C_{2-8}$ alkenyl or benzyl;
  $R_3$ represents $C_{1-8}$ alkyl or $C_{2-8}$ alkenyl;
  $R_1$ and $R_2$ may be the same or different; and $R_3$ may be identical with or different from $R_1$ and/or $R_2$.

2. Process for the preparation of new benzoic acid derivatives of the general Formula I

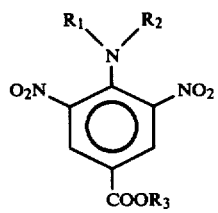

(wherein $R_1$, $R_2$ and $R_3$ are as stated in claim 1) which comprises esterifying 4-chloro-3,5-dinitro-benzoic acid with a saturated or unsaturated aliphatic alcohol at a temperature between 20° C. and 120° C.—preferably at 60°–100° C.—in the presence of a solvent as medium and in the presence of a catalyst; and aminating the ester thus obtained with ammonia or the corresponding primary or secondary amine at a temperature between 40° C. and 100° C.—preferably at 60°–90° C.—in the melt or in an inert solvent as medium, in the presence of an acid binding agent; or changing the order of succession of the said two steps and carrying out at first amination and thereafter esterification.

3. Process according to claim 2 which comprises using in the esterification step a mineral acid or a cation exchanging resin as catalyst.

4. Process according to claim 2 which comprises using in the esterification step an excess of the esterifying alcohol or benzene, toluene, xylene or an other inert solvent as reaction medium.

5. Process according to claims 2 which comprises removing the water formed in the esterification reaction by means of azeotropic distillation.

6. Process according to claim 5 which comprises carrying out azeotropic distillation with the aid of an inert solvent and using 1.2–1.5 moles of alcohol related to 1 mole of 4-chloro-3,5-dinitro-benzoic acid.

7. Process according to claim 2 which comprises using in the amination step an excess of the amine or an organic or inorganic base as acid binding agent.

8. Process according to claim 2 which comprises using an inorganic base as acid binding agent and carrying out the amination reaction in the presence of phosphoric acid or an acidic phosphate salt.

9. Process according to any of claims 2, which comprises carrying out amination in an inert organic solvent or in a mixture of water and a water-inmiscible organic solvent.

10. Process according to claim 9 which comprises using benzene, toluene, xylene, chloroform or an other inert solvent as reaction medium.

11. Benzoic acid derivatives of the general Formula I wherein
  $R_1$ and $R_2$ stand for $C_{1-8}$ alkyl, $C_{2-8}$ alkenyl or benzyl;
  $R_3$ represents $C_{1-8}$ alkyl or $C_{2-8}$ alkenyl;
  $R_1$ and $R_2$ may be the same or different; and $R_3$ may be indentical with or different from $R_1$ and/or $R_2$.

12. n-propyl-4-diallylamino-3,5-dinitro-benzoate.

13. Method for combating fungi and/or weeds pests which comprises applying onto the plants, parts thereof, the corn, the soil or onto the objects to be protected a composition according to claim 1.

* * * * *